United States Patent
Woo

(10) Patent No.: US 11,590,191 B2
(45) Date of Patent: Feb. 28, 2023

(54) A.C.C. EXTRACT HAVING ANTI-INFLAMMATORY AND ANTIMICROBIAL EFFECT AND COMPOSITION COMPRISING SAME AS ACTIVE INGREDIENT

(71) Applicant: NATURE FOUR CO., LTD, Gyeongsan-si (KR)

(72) Inventor: Yong Kyu Woo, Daegu (KR)

(*) Notice: Subject to any disclaimer, the term of this patent is extended or adjusted under 35 U.S.C. 154(b) by 339 days.

(21) Appl. No.: 16/954,670

(22) PCT Filed: Jul. 20, 2018

(86) PCT No.: PCT/KR2018/008250
§ 371 (c)(1),
(2) Date: Jun. 17, 2020

(87) PCT Pub. No.: WO2019/132147
PCT Pub. Date: Jul. 4, 2019

(65) Prior Publication Data
US 2020/0353028 A1    Nov. 12, 2020

(30) Foreign Application Priority Data
Dec. 28, 2017  (KR) .......................... 10-2017-0181881

(51) Int. Cl.
| | | |
|---|---|---|
| *A61K 36/756* | (2006.01) | |
| *A61P 31/04* | (2006.01) | |
| *A61P 29/00* | (2006.01) | |
| *A61K 36/28* | (2006.01) | |
| *A61K 36/355* | (2006.01) | |
| *A61K 36/484* | (2006.01) | |
| *A61K 36/505* | (2006.01) | |
| *A61K 36/534* | (2006.01) | |
| *A61K 36/539* | (2006.01) | |
| *A61K 36/63* | (2006.01) | |
| *A61K 36/65* | (2006.01) | |

(52) U.S. Cl.
CPC ............ *A61K 36/756* (2013.01); *A61K 36/28* (2013.01); *A61K 36/355* (2013.01); *A61K 36/484* (2013.01); *A61K 36/505* (2013.01); *A61K 36/534* (2013.01); *A61K 36/539* (2013.01); *A61K 36/63* (2013.01); *A61K 36/65* (2013.01); *A61P 29/00* (2018.01); *A61P 31/04* (2018.01)

(58) Field of Classification Search
CPC .... A61K 36/756; A61K 36/28; A61K 36/355; A61K 36/484; A61K 36/505; A61K 36/534; A61K 36/539; A61K 36/63; A61K 36/65; A61P 31/04; A61P 29/00
See application file for complete search history.

(56) References Cited

FOREIGN PATENT DOCUMENTS

| JP | 2006124356 A | 5/2006 |
|---|---|---|
| JP | 2016190822 A | 11/2016 |
| KR | 10-2000-0060612 A | 10/2000 |
| KR | 10-2010-0059188 A | 6/2010 |

OTHER PUBLICATIONS

Ryu Jin-hyup et al., Anti-inflammatory effects of ACC extracts in LPS-induced Raw 264.7 cells, Journal of Korea Academia-Industrial, 2017, vol. 18, Issue 12, pp. 503-511 (published on Dec. 31, 2017) p. 505—See 507.
International Search Report for corresponding PCT/KR2018/008250.
Written Opinion of the ISA for corresponding PCT/KR2018/008250.

*Primary Examiner* — Aaron J Kosar
(74) *Attorney, Agent, or Firm* — Egbert, McDaniel & Swartz, PLLC

(57) ABSTRACT

Provided is an A.C.C. extract from a combination of medicinal herbs, which are *Phellodendron* bark, *Scutellaria baicalensis*, *Paeonia lactiflora* Pall, *Dictamnus dasycarpus* Turcz, *Anemarrhena asphodeloides*, Alumen, *Dryobalanops aromatica* Gaertner, *Mentha arvensis* var. piperascens, *Inula helenium*, *Syringa velutina* var. *kamibayashii*, *Corydalis incisa*, *Eclipta prostrata*, *Lonicera japonica*, and *Glycyrrhiza uralensis*, and a composition having the same as an active ingredient. The A.C.C. extract of the present invention reduces production of TNF-α IL-1β and IL-6, thereby regulating the expression of iNOS and thus exhibiting an anti-inflammatory effect inhibiting NO production. Also clinically, the A.C.C. extract of the present invention is a substance that alleviates symptoms such as diaper rash and miliaria through anti-inflammatory and antimicrobial activities and can be used as an effective anti-inflammatory agent.

3 Claims, 3 Drawing Sheets

[Figure 1]
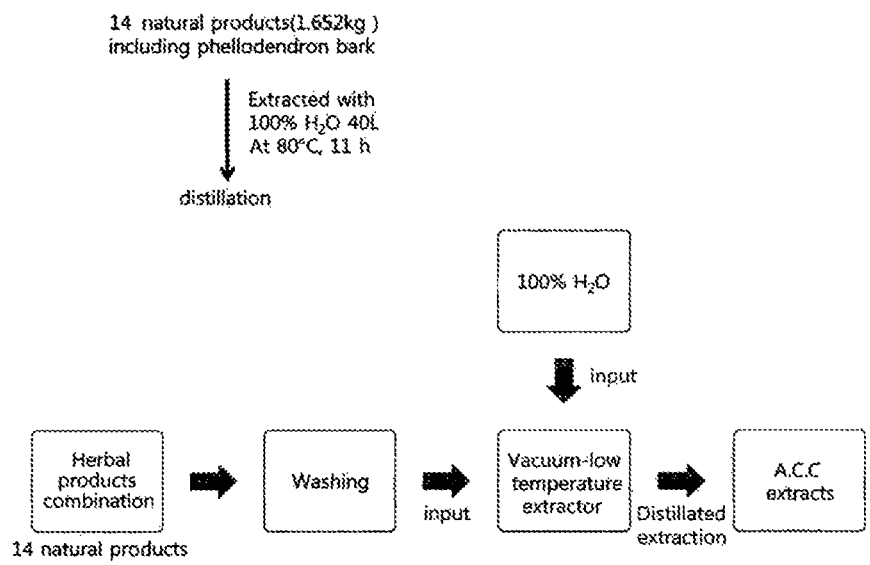
[Figure 2]
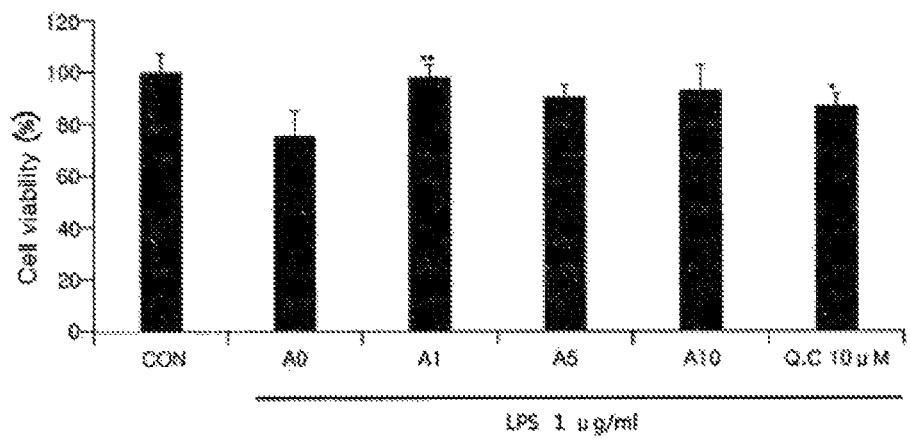

【Figure 3】
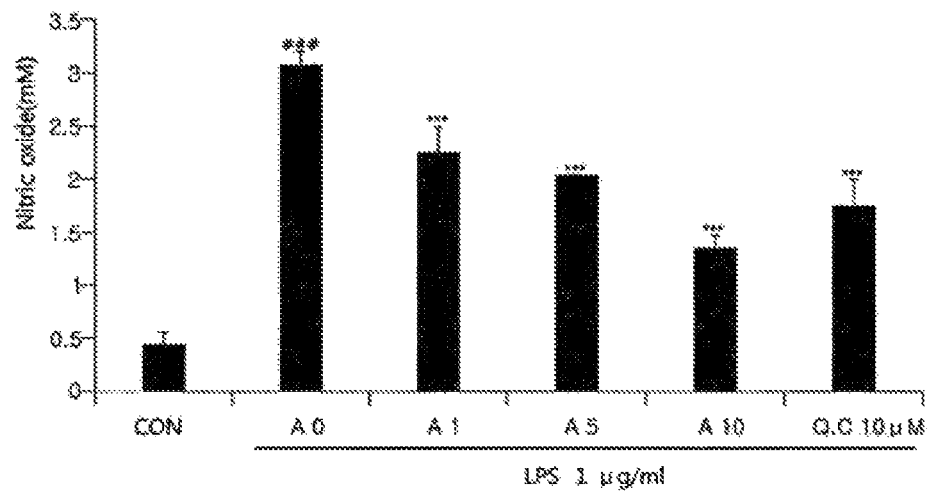
【Figure 4】
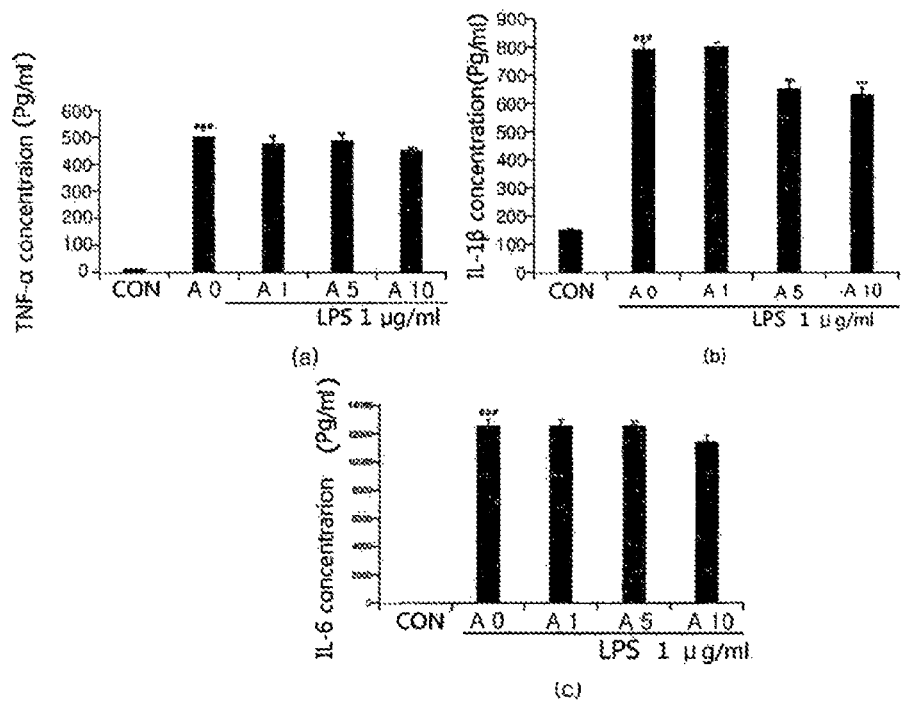

[Figure 5]
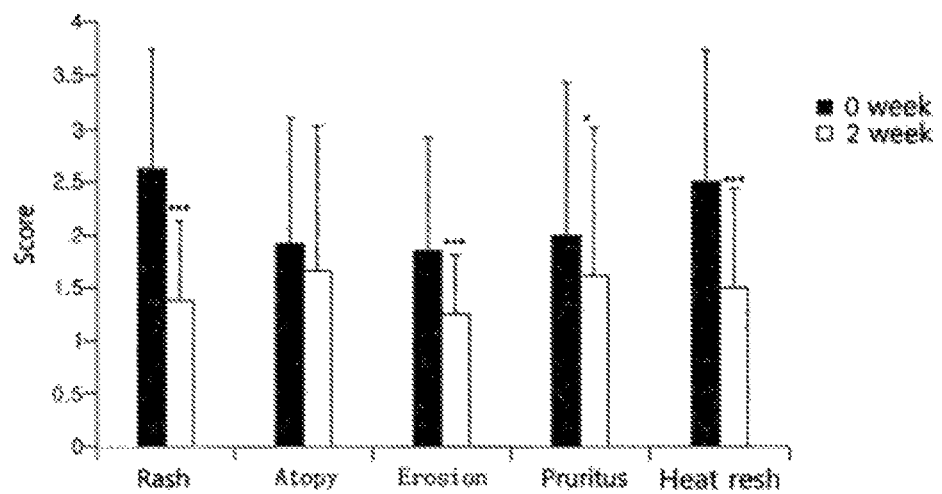

A.C.C. EXTRACT HAVING ANTI-INFLAMMATORY AND ANTIMICROBIAL EFFECT AND COMPOSITION COMPRISING SAME AS ACTIVE INGREDIENT

TECHNICAL FIELD

The present invention relates to an extract having anti-inflammatory and antibacterial effects and an antibacterial and anti-inflammatory composition.

BACKGROUND ART

Inflammatory response occurring in the body is one of the body's defense mechanisms that are important for restoring damaged areas caused by physical and chemical stimuli such as wounds or bacterial infections. When stimulation is applied, vascular active substances are released and vascular permeability increases, causing inflammation. In addition, the inflammatory response is a restoration process that occurs in vivo by external stimuli and is clinically accompanied by redness, fever, swelling, and pain. Cells involved in the inflammatory response include macrophages, monocytes, lymphocytes, mast cells, fibroblasts, platelets, etc., and macrophages are known as major cells that induce inflammatory response. These cells are activated by stimulation or by cytokines secreted from immune cells to produce nitric oxide (NO) and cytokines, which play an important role in biodefense. In addition, during inflammatory response, inflammatory mediators such as histamine, serotonin, arachidonic acid metabolites, reactive oxygen species, cytokines, etc. are produced and released.

Repetitive inflammatory responses also cause excessive generation of reactive oxygen species in inflammatory cells, resulting in permanent genetic modification which results in irreversible lesions. That is, the inflammatory response is a defense mechanism occurring in vivo, but when inflammatory response occurs continuously, it promotes mucosal damage, resulting in edema, pain, redness, fever, etc., and can cause diseases associated with chronic inflammation, such as cardiovascular diseases, rheumatoid arthritis, bronchitis and cancer.

In general, iNOS of nitric oxide synthase (NOS) is known to be involved in inflammatory response, and is expressed by stimulation of interferon-γ, inflammatory cytokines, and LPS. NO in the body plays an important role in antibacterial activity and tumor removal, but NO produced by iNOS is known to induce an increased vascular permeability, edema, etc., and to stimulate the synthesis of inflammatory mediators to exacerbate inflammation.

Lipopolysaccharide (LPS) is well known as an endotoxin in the extracellular membrane of Gram-negative bacteria. It catalyzes inflammatory response by stimulating the secretion of inflammatory-mediated cytokines, such as tumor necrosis factor-α (TNF-α), interleukin-1β (IL-1β) and IL-6, from macrophages or monocytes. TNF-α is a cytokine produced by macrophages, lymphocytes, and white blood cells in the body, and is not produced under normal conditions, but is synthesized and secreted when macrophages are stimulated. IL-6, a representative pro-inflammatory cytokine, is secreted from various types of cells, including monocytes, and plays an important role in the initial immune response. IL-1β constitutes a representative group of inflammatory cytokines along with IL-6 and TNF-α, is a mediator that produces NO, and is known as a cytokine that causes local inflammation, activates T cells, matures B cells and activates NK cells. It has been reported that synthesis of these inflammatory mediators is involved in the process of conversion of arachidonic acid to leukotriene, prostaglandin, thromboxane, etc. by cyclooxygenase (COX) and in the production of nitric oxide (NO), resulting in fatal consequences to the host. Particularly, NO is a highly reactive substance and is known to play an essential role in the innate immune response against pathogens such as bacteria, viruses, fungi, and parasites. NO is produced from L-arginine by NO synthase (NOS). NOS is divided into constitutive NOS (cNOS) and inducible NOS (iNOS). Among them, iNOS is known to produce a large amount of NO by external stimulation or the stimulation of pro-inflammatory cytokines or the like, causing vascular permeability and edema, which induce inflammatory response, and leads to immunological disorders such as rheumatoid arthritis and autoimmune disorders, in severe cases. In this regard, there is a demand for the development of effective anti-inflammatory therapeutic agents along with the development of natural product extracts having anti-bacterial and anti-inflammatory activities.

DISCLOSURE

Technical Problem

An object of the present invention is to provide an extract having antibacterial and anti-inflammatory effects using natural herbal medicines, and particularly, to evaluate the anti-inflammatory activity and clinical efficacy of an A.C.C. extract obtained by distillation extraction of a total of 14 herbal medicines including *Phellodendron* bark.

Another object of the present invention is to confirm that the A.C.C. extract is an active ingredient having a strong antibacterial effect together with an anti-inflammatory effect.

Still another object of the present invention is to confirm that the A.C.C. extract is a clinically effective agent that alleviates symptoms such as diaper rash and heat rash, by exhibiting anti-inflammatory and antibacterial effects, thereby confirming that the A.C.C. extract can be used as an effective agent against inflammatory diseases.

Technical Solution

To solve the above-described problem, the present invention provides an A.C.C. extract from a combination of *Phellodendron* bark, *Scutellaria baicalensis, Paeonia lactiflora* Pall, *Dictamnus dasycarpus* Turcz, *Anemarrhena asphodeloides, Alumen, Dryobalanops aromatica Gaertner, Mentha arvensis* var. piperascens, *Inula helenium, Syringa velutina* var. *kamibayashii, Corydalis incisa, Eclipta prostrata, Lonicera japonica*, and *Glycyrrhiza uralensis* herbal medicines.

In particular, the combination of herbal medicines for preparing the extract may comprise 16 to 24 wt % of *Phellodendron* bark, 1 to 7 wt % of *Scutellaria baicalensis*, 5 to 11 wt % of *Paeonia lactiflora* Pall, 5 to 11 wt % of *Dictamnus dasycarpus* Turcz, 1 to 7 wt % of *Anemarrhena asphodeloides*, 4 to 12 wt % of *Alumen*, 1 to 7 wt % of *Dryobalanops aromatica* Gaertner, 1 to 7 wt % of *Mentha arvensis* var. piperascens, 1 to 7 wt % of *Inula helenium*, 1 to 7 wt % of *Syringa velutina* var. *kamibayashii*, 1 to 7 wt % of *Corydalis incisa*, 1 to 7 wt % of *Eclipta prostrata*, 1 to 7 wt % of *Lonicera japonica*, and 1 to 7 wt % of *Glycyrrhiza uralensis*.

The sample (A.C.C. extract) obtained by distillation extraction of a total of 14 herbal medicines including *Phellodendron* bark may have antibacterial and anti-inflammatory activities. In an experiment for the sample, the amount of nitric oxide (NO) produced by RAW 264.7 cells stimulated with lipopolysaccharide (LPS) and changes in the production of inflammatory cytokines such as tumor necrosis factor (TNF)-α, interleukin (IL)-1β and IL-6 were examined. The results showed that A.C.C. extract strongly inhibited the LPS-induced production of NO and inflammatory cytokines without cytotoxicity.

In addition, the A.C.C. extract of the present invention may have antibacterial effects against *Pseudomonas aeruginosa*, *Staphylococcus aureus*, MRSA (methicillin-resistant *Staphylococcus aureus*), *Candida albicans* and *Streptococcus mutans* bacteria. The A.C.C. extract showed strong bacterial reduction rates of 99.9% in the bacteria, suggesting that the A.C.C. extract is an active ingredient having a strong antibacterial effect together with an anti-inflammatory effect.

In the related experiment, the antibacterial activities of the A.C.C. extract against *Pseudomonas aeruginosa*, *Staphylococcus aureus*, MRSA (methicillin-resistant *Staphylococcus aureus*), *Candida albicans* and *Streptococcus mutans* strains were confirmed, and for clinical applications, the A.C.C. extract was applied to infants and toddlers who were suffering from diaper rash, itching, and heat rash symptoms. As a result, it could be confirmed that the A.C.C. extract exhibited the effect of improving symptoms, including rash, atopy, erosion, pruritus, and heat rash. In addition, it could be visually confirmed that heat rash on the skin of the infants and toddlers was considerably ameliorated after 2 weeks. These results confirm that the A.C.C. extract is a clinically effective agent that alleviates symptoms such as diaper rash and heat rash, by exhibiting anti-inflammatory and antibacterial effects, and that the A.C.C. extract may be an effective alternative against inflammatory diseases.

Another aspect of the present invention provides an anti-bacterial and anti-inflammatory composition containing the A.C.C. extract as an active ingredient. The A.C.C. extract exhibits a synergy of anti-inflammatory effect and antibacterial effect, and thus may be used as an effective agent for treating inflammation.

Advantageous Effects

The A.C.C. extract obtained by distillation extraction of a total of 14 herbal medicines including *Phellodendron* bark has a strong antibacterial effect together with an anti-inflammatory effect.

In addition, the A.C.C. extract of the present invention exhibits an anti-inflammatory effect of inhibiting NO production by controlling the expression of iNOS through decreasing the production of TNF-α, IL-1β and IL-6.

Therefore, the A.C.C. extract of the present invention is a clinically effective agent that alleviates symptoms such as diaper rash and heat rash, by exhibiting anti-inflammatory and antibacterial effects, and may be used as an effective agent for treating inflammation.

DESCRIPTION OF DRAWINGS

FIG. 1 is a schematic view showing distillation extraction of 14 natural products including *Phellodendron* bark.

FIG. 2 is a graph showing the results of an MTT assay performed to analyze the toxicity of an A.C.C. extract on Raw 264.7 cells treated with LPS. (*, $p<0.05$, **, $p<0.01$ compared to control. Con; control, LPS 1 μg/ml; 1 μg/ml; 1 μg/ml lipopolysaccharide, A0; LPS 1 μg/ml, A1; A.C.C. 1 μg/ml, A5; A.C.C. 5 μg/ml, A10; A.C.C. 10 μg/ml, Q.C 10 μM; quercetin 10 μM).

FIG. 3 is a graph showing that the LPS-induced increase in NO production in Raw 264.7 cells is inhibited by the A.C.C. extract in a concentration-dependent manner. (###, $p<0.001$ compared to control and ***, $p<0.001$ compared to 1 μg/ml LPS. Con; control, LPS 1 μg/ml; 1 μg/ml lipopolysaccharide, A0; LPS 1 μg/ml, A1; A.C.C. 1 μg/ml, A5; A.C.C. 5 μg/ml, A10; A.C.C. 10 μg/ml, Q.C 10 μM; quercetin 10 μM).

FIG. 4 depicts graphs showing that the effect of the A.C.C. extract on the inhibition of cytokine production in Raw 264.7 cells.

(a) Effects of A.C.C. extracts on TNF-α in dose-dependent manner.

(b) Effects of A.C.C. extracts on IL-1β in dose-dependent manner.

(c) Effects of A.C.C. extracts on IL-6 in dose-dependent manner.

Pro-inflammatory cytokines were measured in media of Raw 264.7 cells stimulated with LPS. ###, $p<0.001$ compared to control, and , $p<0.01$, and *, $p<0.001$ compared to 1 μg/ml LPS. Con; control, LPS 1 μg/ml; 1 μg/ml lipopolysaccharide, A0; LPS 1 μg/ml, A1; A.C.C. 1 μg/ml, A5; A.C.C. 5 μg/ml, A10; A.C.C. 10 μg/ml.

FIG. 5 is a graph showing the changes in symptoms, such as diaper rash and heat rash, after the use of the A.C.C. extract. (n=18). *, $p<0.05$, and ***, $p<0.001$ compared to 0 week.

MODE FOR INVENTION

Hereinafter, the present invention will be described in more detail through examples. However, these examples are merely illustrative of the present invention, and the scope of the present invention is not limited to these examples.

Example 1. Selection of Materials and Preparation of A.C.C. Extract

A total of 14 herbal medicines were selected by conducting a literature search based on herbal medicine. The herbal medicines used were purchased as packaged herbal medicines from CK Co., Ltd. in Seoul Yangnyeong Market. Dulbecco's Modified Eagle's Medium (DMEM) and fetal bovine serum (FBS) were purchased from Hyclone (Logan, Utah, USA). Penicillin (100 U/ml) and streptomycin (100 μg/ml) were purchased from Gibco (Life technology Inc., Gaithersburg, Md., USA). LPS, 3-(4,5-dimethylthiazol-2-yl)-2,5-diphenyl tetrazolium bromide (MTT), sodium nitrite, and dimethyl sulfoxide (DMSO) were purchased from Sigma Chemical Co. (St. Louis, Mo., USA). A nitric oxide (NO) detection kit was purchased from iNtron, and an ELISA assay kit was purchased from Thermo Fisher Scientific.

*Phellodendron* bark and 13 other herbal medicines were combined according to the respective proportions and subjected to distillation extraction using 40 L of triple distilled water as a solvent at 80° C. for 11 hours (see FIG. 1 and Table 1).

TABLE 1

Materials and proportions in A.C.C. extract

| Materials | Proportion (%) |
|---|---|
| *Phellodendron* bark | 20 ± 4 |
| *Scutellaria baicalensis* | 4 ± 3 |
| *Paeonia lactiflora* Pall | 8 ± 3 |
| 8*ictamnus dasycarpus* Turcz | 8 ± 3 |
| *Anemarrhena asphodeloides* | 4 ± 3 |
| Alumen | 8 ± 3 |
| *Dryobalanops aromatica* Gaertner | 4 ± 3 |
| *Mentha arvensis* var. piperascens | 4 ± 3 |
| *Inula helenium* | 4 ± 3 |
| *Syringa velutina* var. kamibayashii | 4 ± 3 |
| *Corydalis incisa* | 4 ± 3 |
| *Eclipta prostrata* | 4 ± 3 |
| *Lonicera japonica* | 4 ± 3 |
| *Glycyrrhiza uralensis* | 4 ± 3 |

Experimental Example 1: Measurement of Cytotoxicity by MTT Assay

Culture of Raw 264.7 Cells

Raw 264.7 cells were purchased from the Korean Cell Line Bank. The cells were cultured in a DMEM medium containing 100 units/ml of penicillin/streptomycin and 10% FBS in an incubator at 37° C. under 5% $CO_2$, and passaged once every 3 days.

For measurement of the viability of Raw 264.7 cells, the cells were seeded into a 96-well plate at a density of $2 \times 10^4$ cells/well, and then stabilized by 24 hours of culture. After 24 hours, the medium was completely removed from each well. The A.C.C. extract was diluted in a medium to final concentrations of 1, 5 and 10 µg/ml, and the cells were treated with the medium, and then cultured for 3 hours. After 3 hours, the wells excluding a control were treated with 1 µg/ml of LPS. After 24 hours, the medium was completely removed. Subsequently, 100 µL of MTT solution (0.2 µg/ml in phenol red free DMEM) was added to each well and incubated in an incubator at 37° C. under 5% $CO_2$ for 2 hours so that the MTT was reduced. Thereafter, DMSO solution was added to each well to dissolve the produced formazan. The absorbance at 545 nm was measured using a microplate reader.

Experimental Example 2: Measurement of Nitric Oxide Production

Raw 264.7 cells were added to a 6-well plate at a density of $1 \times 10^5$ cells/well. After incubation in an incubator at 37° C. under 5% $CO_2$ for 24 hours, the Raw 264.7 cells were treated with 1, 5 and 10 µg/ml of the A.C.C. extract, and after 3 hours, treated with 1 µg/ml of LPS and cultured for 24 hours. Nitric oxide was analyzed by a nitric oxide (NO) detection kit (iNtron) based on the Griess reaction. Griess reagent was added to and mixed with the cell culture supernatant and incubated at room temperature for 10 minutes, and then the absorbance at 520 nm was measured using a microplate reader. Based on a standard curve of sodium nitrite, the NO concentration in the culture medium was determined using the following equation.

Experimental Example 3: Measurement of Inflammation-Related Cytokine Secretion To measure the production of the pro-inflammatory cytokines TNF-α, IL-6 and IL-1β, Raw 264.7 cells were added to a 6-well plate at a density of $1 \times 10^5$ cells/well. After 24 hours, the cells were treated with 1, 5 and 10 µg/ml of the A.C.C. extract, and after 3 hours, all the wells excluding a control were treated with 1 µg/ml of LPS. After 24 hours of culture, the amounts of TNF-α, IL-6 and IL-1β secreted into the medium were analyzed using an ELISA kit (Thermo Fisher Scientific). The absorbance at 450 nm was measured using a microplate reader.

Experimental Example 4: Measurement of Antibacterial Activity

To examine the antibacterial activity of the A.C.C. extract, the antibacterial activity was measured using the paper disc method. Before testing, each cultured test strain was inoculated into each medium at a concentration of $1.0 \times 10^4$ CFU/ml or more. Each sterilized paper disc was loaded with 100 µL of the A.C.C. extract and dried for 30 minutes. The paper disc loaded with the A.C.C. extract was placed on each medium inoculated with each test strain, and then incubated in an incubator for 24 to 48 hours. The inhibition zone around the paper disk was measured and result evaluation and analysis was conducted.

Experimental Example 5: Clinical Study

For the subjects recruited through announcement, the agents (guardians) answered the 'preliminary questionnaire' according to the characteristics of the subjects. After checking the symptoms, skin conditions, etc. through preliminary questionnaire survey, the composition was provided, and the researcher trained the agents to apply the composition to each subject 5 to 10 times in an amount of 1 cc per day at the same time every day for 14 days. In addition, for objective research results, the affected area was photographed and comparative analysis between before and after the application was performed. In this case, a photograph of the area that can identify an individual, such as a face, was excluded. After 14 days of the application, the agents answered the "test questionnaire". The data will be stored according to the Bioethics Act for 3 years from the time the study was completed, and after the data storage period, personal information and photographs will be permanently deleted such that they cannot be restored.

Experimental Example 6: Statistical Analysis

All measured values were expressed as mean±standard deviation values, and statistical analysis was appropriately performed through two-sided independent-sample t-test or ANOVA test. When this analysis showed a significant difference in the group mean value between groups, Scheff's test was performed as a post-hoc test.

EXPERIMENTAL RESULTS

1. Cytotoxicity of A.C.C. Extract on Raw 264.7 Cells

In order to examine the effect of the A.C.C. extract on Raw 264.7 cells, the cells were pretreated with various concentrations (1, 5, and 10 µg/ml) of the A.C.C. extract, and then treated with 1 µg/ml of LPS. After 24 hours of culture, cytotoxicity was analyzed using an MTT assay. As a result, it was confirmed that the cells showed high cell viabilities of 98.47, 90.91 and 92.23%, respectively, which showed no significant significance in cell survival (FIG. 2).

2. Effect of A.C.C. Extract on Inhibition of NO Production in Raw 264.7 Cells When macrophages are stimulated with LPS, inducible nitric oxide synthase (iNOS) is expressed to produce an excessive amount of NO. The produced NO is known to cause tissue damage by promoting inflammatory response. Thus, whether the A.C.C. extract inhibits inflammatory mediators such as NO was examined. As a result, it was confirmed that when Raw 264.7 cells were treated with LPS, NO production in the cells increased 7-fold (from 0.45 to 3.15) compared that in the control. In addition, Raw 264.7 cells were treated with 1, 5 and 10 μg/ml of the A.C.C. extract and the effect of the A.C.C. extract on the inhibition of NO production was evaluated, and as a result, it was confirmed that the LPS-induced production of NO in the Raw 264.7 cells was inhibited by the A.C.C. extract in a manner dependent on the concentration of the A.C.C. extract (see FIG. 3).

3. Effect of A.C.C. Extract on Inhibition of Cytokine Production in Raw 264.7 Cells When inflammatory response is induced, the production of inflammatory mediators such as NO and PGE2, and inflammatory cytokine production mediated by the inflammatory response, occurs. Representative cytokines include TNF-α, IL-1β and IL-6. In order to examine how the A.C.C extract affects inflammation mediating cytokines, changes in TNF-α, IL-1β and IL-6 were measured by an ELISA assay. When Raw 264.7 cells were treated with LPS, TNF-α, IL-1β and IL-6 in the Raw 264.7 cells significantly increased compared to those in the control (FIG. 4). However, when the Raw 264.7 cells were treated with 10 μg/ml of the A.C.C. extract, TNF-α, IL-1β and IL-6 in the Raw 264.7 cells significantly decreased. From these results, it was confirmed that the A.C.C. extract exhibits an anti-inflammatory effect by inhibiting inflammation-inducing cytokines in Raw 264.7 cells.

4. Antibacterial Activities and Effects of A.C.C. Extract

As main bacteria causing itching and rash in children, group A *Streptococcus pyogenes* and *Staphylococcus aureus* are known. In addition, main fungi causing vaginal candidiasis, rash and itchy sense include *Candida albicans*, and for this reason, for men, areas with folded skin and high humidity are infected with fungi, skin infections, such as jock itch or Candidal intertrigo, may occur. In this experimental example, an experiment was performed on *Pseudomonas aeruginosa*, *Staphylococcus aureus*, MRSA (Methicillin-resistant *Staphylococcus aureus*), *Candida albicans* and *Streptococcus mutans* bacteria according to the method shown in Table 2 below, and as a result, the A.C.C. extract showed a strong bacteria reduction rate of 99.9% in a total of five bacteria types (Table 2).

TABLE 2

Antibacterial Activities and effects of A.C.C. extract

| | | Results | | | |
|---|---|---|---|---|---|
| Bacteria | | Initial conc. (CFU/ml) | Conc. after 24 h (CFU/ml) | Inhibition rate(%) | Condition |
| *Pseudomonas aeruginosa* | Control | $1.2 \times 10^4$ | $2.3 \times 10^5$ | — | 37 ± 0.2° C. |
| | A.C.C. | $1.2 \times 10^4$ | <10 | 99.9 | |
| *Staphylococcus aureus* | Control | $3.6 \times 10^4$ | $7.5 \times 10^5$ | — | |
| | A.C.C. | $3.6 \times 10^4$ | <10 | 99.9 | |
| MRSA (Methicillin-resistant *Staphylococcus aureus*) | Control | $1.0 \times 10^4$ | $2.4 \times 10^4$ | — | |
| | A.C.C. | $1.0 \times 10^4$ | <10 | 99.9 | |
| *Candida albicans* | Control | $3.8 \times 10^4$ | $1.7 \times 10^5$ | — | |
| | A.C.C. | $3.8 \times 10^4$ | <10 | 99.9 | |
| *Streptococcus mutans* | Control | $2.2 \times 10^4$ | $3.9 \times 10^5$ | — | |
| | A.C.C. | $2.2 \times 10^4$ | <10 | 99.9 | |

Thus, it can be seen that the A.C.C. extract is an active ingredient having strong activity against the above-described five types of bacteria.

5. Effect of A.C.C. Extract Against Diaper Rash and Heat Rash in Infants and Toddlers A clinical test was performed to examine whether symptoms such as rash, atopy, erosion, pruritus and heat rash were alleviated when the A.C.C extract was applied to the infants and toddlers who were suffering from diaper rash, pruritus and heat rash symptoms. Before the clinical test, a preliminary questionnaire was conducted with a total of five items: rash, atopy, erosion, pruritus, and heat rash. The preliminary questionnaire was conducted on a 4-point scale, and as a result, rash showed the highest score (2.61±1.1) and heat rash showed the second highest score (2.41±1.1). After the preliminary questionnaire was completed, the extract was applied in an amount of 1 cc 5-10 times a day at the same time every day for 14 days. After 14 days, the test questionnaire was conducted. As a result, the scores after use were all 1.5 or less, indicating that the symptoms were generally alleviated. The scores of rash and heat rash, which were the highest before use of the extract, significantly decreased to 1.39±0.70 and 1.35±0.70, respectively (FIG. 5 and Table 3). In addition, the symptoms before the clinical test for the infants and toddlers and after 1 week of application of the A.C.C extract and after 2 weeks of application of the A.C.C extract were comparatively observed. As a result, it could be confirmed that heat rash on the skin was considerably alleviated after 2 weeks. Thus, it appears that the A.C.C. extract is effective against symptoms such as rash and heat rash.

TABLE

Effect of A.C.C. extract of diaper rash
and heat rash in infants and toddlers

|  | 0 weeks (average ± SD) | 2 weeks (average ± SD) |
|---|---|---|
| Rash | 2.611 ± 1.092 | 1.388 ± 0.697 |
| Atopy | 1.888 ± 1.182 | 1.611 ± 1.195 |
| Erosion | 1.777 ± 0.808 | 1.167 ± 0.514 |
| Pruritus | 2.055 ± 1.211 | 1.611 ± 1.195 |
| Heat rash | 2.411 ± 1.064 | 1.352 ± 0.702 |

Looking at the results of the experiments performed in the present invention, it can be confirmed that the A.C.C. extract is not toxic to mouse macrophage Raw 264.7 cells (FIG. 2), suggesting that the effects of the A.C.C. extracts in the cells are unique effects independent of the viability of the cells. To evaluate the anti-inflammatory effect of the A.C.C. extract, Raw 264.7 cells were pre-treated with various concentrations of the A.C.C. extract for 3 hours and treated with 1 μg/ml of LPS for 24 hours, and then the change in the production of the inflammatory mediator NO in the cells was measured. As a result, it was confirmed that the LPS-induced production of NO was decreased by the A.C.C. extract in a manner dependent on the concentration of the A.C.C. extract (FIG. 3).

This result indicates that the A.C.C. extract exhibits anti-inflammatory activity by inhibiting the formation of the important inflammatory mediator NO in the LPS-induced inflammatory process.

In addition, it is known that when inflammatory response begins, NF-κB known as an inflammatory response transcription factor is activated to regulate the gene expression of important inflammation-promoting proteins such as TNF-α, IL-1β and IL-6, which play an important role in inflammatory response by controlling the activation of iNOS. Thus, an examination was made of the effect of the A.C.C. extract on inflammation-mediating cytokines (TNF-α, IL-1β and IL-6) which are important inflammatory markers. Specifically, Raw 264.7 cells were treated with LPS to induce inflammation, and an examination was made of how the A.C.C. extract changes the production of TNF-α, IL-1β and IL-6. As a result, it could be seen that the A.C.C. extract strongly inhibited LPS-induced inflammatory mediators in a manner depending on the concentration thereof (FIG. 4).

Through these results, it is evident that the A.C.C. extract exhibits an anti-inflammatory effect of inhibiting NO production by controlling the expression of iNOS through decreasing the production of TNF-α, IL-1β and IL-6. In addition, the A.C.C. extract showed a strong bacteria reduction rate of 99% against *Pseudomonas aeruginosa*, *Staphylococcus aureus*, MRSA (Methicillin-resistant *Staphylococcus aureus*), *Candida albicans* and *Streptococcus mutans* bacteria (Table 1). This indicating that the A.C.C. extract can be used as an effective anti-inflammatory agent showing a synergy of anti-inflammatory effect and antibacterial effect. To confirm this clearly, a test was performed to examine whether symptoms such as rash, atopy, erosion, pruritus and heat rash were alleviated when the A.C.C extract was applied to the infants and toddlers who were suffering from diaper rash, pruritus and heat rash symptoms. A preliminary questionnaire was conducted on a 4-point scale, and as a result, rash showed the highest score (2.61±1.1). After 14 days of application of the A.C.C extract, the score of rash was 1.39±0.70, which significantly decreased compared to that before application (FIG. 5). In addition, the symptoms before and after the clinical test for the infants and toddlers were observed, and as a result, it could be confirmed that when the A.C.C. extract was applied for 2 weeks, heat rash on the skin was considerably alleviated. This confirms that the A.C.C. extract is a clinically effective agent that alleviates symptoms such as diaper rash and heat rash by exhibiting anti-inflammatory and antibacterial effects. Therefore, the A.C.C. extract having anti-inflammatory and antibacterial effects and a product comprising the same as an active ingredient can become an effective alternative against inflammatory diseases.

The invention claimed is:

1. An antibacterial and anti-inflammatory composition comprising:
    16 wt %-24 wt % of an extract of *Phellodendron* bark;
    1 wt %-7 wt % of an extract of *Scutellaria baicalensis*;
    5 wt %-11 wt % of an extract of *Paeonia lactiflora* Pall;
    5 wt %-11 wt % of an extract of *Dictamnus dasycarpus* Turcz;
    1 wt %-7 wt % of an extract of *Anemarrhena asphodeloides*;
    4 wt %-12 wt % of an extract of Alumen;
    1 wt %-7 wt % of an extract of *Dryobalanops aromatica* Gaertner;
    1 wt %-7 wt % of an extract of *Mentha arvensis* var. piperascens;
    1 wt %-7 wt % of an extract of *Inula helenium*;
    1 wt %-7 wt % of an extract of *Syringa velutina* var. kamibayashii;
    1 wt %-7 wt % of an extract of *Corydalis incisa*;
    1 wt %-7 wt % of an extract of *Eclipta prostrata*;
    1 wt %-7 wt % of an extract of *Lonicera japonica*; and
    1 wt %-7 wt % of an extract of *Glycyrrhiza uralensis*,
    wherein the extracts of the *Phellodendron* bark, the *Scutellaria baicalensis*, the *Paeonia lactiflora* Pall, the *Dictamnus dasycarpus* Turcz, the *Anemarrhena asphodeloides*, the Alumen, the *Dryobalanops aromatica* Gaertner, the *Mentha arvensis* var. piperascens, the *Syringa velutina* var. kamibayashii, the *Corydalis incisa*, the *Eclipta prostrata*, the *Lonicera japonica* and the *Glycyrrhiza uralensis* are mixed together and in which the total weight percentage does not exceed 100 wt %.

2. A composition for treatment of *Pseudomonas aeruginosa*, *Staphylococcus aureus*, *Candida albicans* and *Streptococcus mutans* bacteria, the composition comprising:
    16 wt %-24 wt % of an extract of *Phellodendron* bark;
    1 wt %-7 wt % of an extract of *Scutellaria baicalensis*;
    5 wt %-11 wt % of an extract of *Paeonia lactiflora* Pall;
    5 wt %-11 wt % of an extract of *Dictamnus dasycarpus* Turcz;
    1 wt %-7 wt % of an extract of *Anemarrhena asphodeloides*;
    4 wt %-12 wt % of an extract of Alumen;
    1 wt %-7 wt % of an extract of *Dryobalanops aromatica* Gaertner;
    1 wt %-7 wt % of an extract of *Mentha arvensis* var. piperascens;
    1 wt %-7 wt % of an extract of *Inula helenium*;
    1 wt %-7 wt % of an extract of *Syringa velutina* var. kamibayashii;
    1 wt %-7 wt % of an extract of *Corydalis incisa*;
    1 wt %-7 wt % of an extract of *Eclipta prostrata*;
    1 wt %-7 wt % of an extract of *Lonicera japonica*; and
    1 wt %-7 wt % of an extract of *Glycyrrhiza uralensis*,
    wherein the extracts of the *Phellodendron* bark, the *Scutellaria baicalensis*, the *Paeonia lactiflora* Pall, the *Dictamnus dasycarpus* Turcz, the *Anemarrhena aspho-

*deloides*, the Alumen, the *Dryobalanops aromatica* Gaertner, the *Mentha arvensis* var. piperascens, the *Syringa velutina* var. *kamibayashii*, the *Corydalis incisa*, the *Eclipta prostrata*, the *Lonicera japonica* and the *Glycyrrhiza uralensis* are mixed together and in which the total weight percentage does not exceed 100 wt %.

3. A composition that decrease production of pro-inflammatory cytokines TNF-α, IL-1β and IL-6 so as to produce an anti-inflammatory effect, the composition comprising:

16 wt %-24 wt % of an extract of *Phellodendron* bark;
1 wt %-7 wt % of an extract of *Scutellaria baicalensis*;
5 wt %-11 wt % of an extract of *Paeonia lactiflora* Pall;
5 wt %-11 wt % of an extract of *Dictamnus dasycarpus* Turcz;
1 wt %-7 wt % of an extract of *Anemarrhena asphodeloides*;
4 wt %-12 wt % of an extract of Alumen;
1 wt %-7 wt % of an extract of *Dryobalanops aromatica* Gaertner,
1 wt %-7 wt % of an extract of *Mentha arvensis* var. piperascens;
1 wt %-7 wt % of an extract of *Inula helenium*;
1 wt %-7 wt % of an extract of *Syringa velutina* var. *kamibayashii*;
1 wt %-7 wt % of an extract of *Corydalis incisa*;
1 wt %-7 wt % of an extract of *Eclipta prostrata*;
1 wt %-7 wt % of an extract of *Lonicera japonica*; and
1 wt %-7 wt % of an extract of *Glycyrrhiza uralensis*,
wherein the extracts of the *Phellodendron* bark, the *Scutellaria baicalensis*, the *Paeonia lactiflora* Pall, the *Dictamnus dasycarpus* Turcz, the *Anemarrhena asphodeloides*, the Alumen, the *Dryobalanops aromatica* Gaertner, the *Mentha arvensis* var. piperascens, the *Syringa velutina* var. *kamibayashii*, the *Corydalis incisa*, the *Eclipta prostrata*, the *Lonicera japonica* and the *Glycyrrhiza uralensis* are mixed together and in which the total weight percentage does not exceed 100 wt %.

\* \* \* \* \*